United States Patent
Single (10) Patent No.: US 8,805,523 B2
(45) Date of Patent: Aug. 12, 2014

(54) BATTERY LIFE OPTIMIZER

(71) Applicant: Peter Scott Single, Lane Cove (AU)

(72) Inventor: Peter Scott Single, Lane Cove (AU)

(73) Assignee: Cochlear Limited, Macquarie University, NSW (AU)

( * ) Notice: Subject to any disclaimer, the term of this patent is extended or adjusted under 35 U.S.C. 154(b) by 42 days.

(21) Appl. No.: 13/709,205

(22) Filed: Dec. 10, 2012

(65) Prior Publication Data

US 2013/0103114 A1    Apr. 25, 2013

Related U.S. Application Data

(62) Division of application No. 10/962,459, filed on Oct. 13, 2004, now Pat. No. 8,334,677.

(30) Foreign Application Priority Data

Oct. 13, 2003 (AU) .................... 2003905571

(51) Int. Cl.
*A61N 1/378* (2006.01)

(52) U.S. Cl.
CPC .................... *A61N 1/378* (2013.01)
USPC ............................................ 607/57

(58) Field of Classification Search
USPC ........... 607/29, 33, 34, 57; 320/130, 132, 149
See application file for complete search history.

(56) References Cited

U.S. PATENT DOCUMENTS

| | | | |
|---|---|---|---|
| 5,411,537 A * | 5/1995 | Munshi et al. .................. 607/33 |
| 5,522,865 A | 6/1996 | Schulman et al. |
| 6,227,204 B1 | 5/2001 | Baumann et al. |
| 6,278,258 B1 | 8/2001 | Echarri et al. |
| 6,333,619 B1 | 12/2001 | Chavez et al. |
| 6,480,003 B1 * | 11/2002 | Ugaji et al. .................... 324/430 |
| 6,553,263 B1 * | 4/2003 | Meadows et al. ............... 607/61 |
| 6,664,764 B1 * | 12/2003 | Odaohhara .................... 320/132 |
| 7,167,756 B1 | 1/2007 | Torgerson et al. |
| 2001/0031909 A1 | 10/2001 | Faltys et al. |
| 2002/0076071 A1 * | 6/2002 | Single ........................... 381/312 |
| 2003/0076113 A1 | 4/2003 | Valenta et al. |
| 2003/0114899 A1 * | 6/2003 | Woods et al. .................... 607/60 |
| 2003/0171787 A1 * | 9/2003 | Money et al. .................... 607/57 |
| 2003/0191504 A1 | 10/2003 | Meadows et al. |
| 2004/0066171 A1 * | 4/2004 | Mori ............................ 320/132 |

FOREIGN PATENT DOCUMENTS

EP    0831674    3/1998
WO    0139830    6/2001

* cited by examiner

*Primary Examiner* — Christopher D Koharski
*Assistant Examiner* — Jeremiah Kimball
(74) *Attorney, Agent, or Firm* — K&L Gates, LLP (57) ABSTRACT

A method of controlling charging of a battery (16) of a totally implantable auditory prosthesis and a control system (50) therefor. The method comprises determining a first charge related characteristic of the battery (16) such as the predetermined minimum amount of charge (58), and a second charge related battery characteristic such as the preset charge level or charge rate of the battery (16). The method further comprises detecting when a charge cycle of the battery (16) commences and monitoring where the charge level of the battery (16) is in relation to the first charge related battery characteristic when the charge cycle commences and adjusting the second charge related battery characteristic depending on the relationship between the charge level and the first charge related battery characteristic at the commencement of the charge cycle. The control system and method has the potential to increase the operational life of the battery (16).

18 Claims, 4 Drawing Sheets

BATTERY LIFE OPTIMIZER

CROSS-REFERENCE TO RELATED APPLICATIONS

This application is a divisional application of U.S. application Ser. No. 10/962,459 filed Oct. 13, 2004, which claims priority from Australian Provisional Patent Application No. 2003905571 filed on Oct. 13, 2003, the contents of which is incorporated herein by reference.

BACKGROUND

1. Field of the Invention

This invention relates to an implanted auditory prosthesis. The invention relates particularly, but not necessarily exclusively, to a method of, and a control system for, charging of a battery of a totally implantable auditory prosthesis such as a cochlear implant or an implanted hearing aid.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often helped by use of conventional hearing aids which amplify sound so that acoustic information reaches the cochlea and the hair cells.

In many people who are profoundly deaf, however, the reason for their deafness is sensorineural hearing loss. This type of hearing loss is due to the absence of, or destruction of, the hair cells in the cochlea, which convert acoustic signals into nerve impulses. These people are thus unable to derive suitable benefit from conventional hearing aid systems, no matter how loud the acoustic stimulus is made, because there is damage to, or absence of, the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve.

Typically, cochlear implant systems consist essentially of two components, an external component, commonly referred to as a processor unit and an internal, implanted component, commonly referred to as a stimulator/receiver unit, the latter receiving signals from the processor unit to provide the sound sensation to a user.

The external component includes a microphone for detecting sounds, such as speech and environmental sounds, a speech processor that converts speech into a coded signal, a power source, for example a battery, and an external transmitter antenna coil.

The coded signal output by the sound processor is transmitted transcutaneously to the implanted stimulator/receiver unit situated within a recess of the temporal bone of the user. This transcutaneous transmission occurs via the external transmitter antenna coil which is positioned to communicate with an implanted receiver antenna coil of the stimulator/receiver unit. Therefore, the communication serves two essential purposes; firstly to transmit, transcutaneously, the coded signal and, secondly, to provide power to the implanted stimulator/receiver unit. The transcutaneous link is, normally, in the form of an RF link, but other links have been proposed and implemented with varying degrees of success.

The implanted stimulator/receiver unit includes, in addition to the receiver antenna coil that receives the coded signal and possibly power from the external processor component, a stimulator that processes the coded signal and outputs a stimulation signal to an intracochlear electrode assembly which applies the electrical stimulation via the basilar membrane to the auditory nerve producing a hearing sensation corresponding to the originally detected sound.

Recently, the Applicant has developed a totally implantable cochlear implant where all the components, including the microphone, are implanted subcutaneously. This results in a more versatile system providing the recipient with greater freedom and ability to use the implant in what would previously have been regarded as adverse environments, eg. wet environments. The Applicant's implant is described in greater detail in PCT/AU01/00769 which is incorporated herein by reference. The implant is powered by an implantable rechargeable battery which receives charging signals, when required, transcutaneously via an external charging device and an implanted receiver antenna coil. Because the battery is part of an implanted system, there is a need to make the battery life as long as possible to reduce the frequency of explantation and/or re-implantation of the implant for the purposes of battery replacement.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect of the invention, there is provided a method of controlling charging of a battery of a totally implantable auditory prosthesis, the method comprising:

determining a first charge related battery characteristic;

determining a second charge related battery characteristic;

detecting when a charge cycle of the battery commences; and monitoring where the charge level of the battery is in relation to the first charge related battery characteristic when the charge cycle commences and adjusting the second charge related battery characteristic depending on the relationship between the charge level and the first charge related battery characteristic at the commencement of the charge cycle.

For ease of explanation, the first charge related battery characteristic is sometimes referred to in this specification as a "safety margin" of the battery. This safety margin may be a predetermined minimum amount of charge contained in the battery.

In one embodiment of the invention, the second charge related battery characteristic may be a preset charge level of the battery. The preset charge level may be determined such that it is lower than a maximum possible state-of-charge of the battery. The battery may be charged to this preset charge level and, in so doing, due to the fact that the battery is not consistently being charged to its maximum battery charge, the life of the battery may be extended, because side reactions are thereby minimised.

When a charge cycle commences, the method may include monitoring the charge level of the battery relative to the safety margin. If the charge level at which charging commences is higher than the safety margin, the method may include lowering the preset charge level. This may occur each time that, when a charge cycle commences, the charge level of the battery is greater than the safety margin. If, however, upon commencement of a charge cycle the charge level of the battery is lower than the safety margin, the method may include, initially, increasing the preset charge level.

Typically, the method may include setting the safety margin to be a voltage corresponding to a charge required for use of the implant for a predetermined period of time. The period of time may, for example, be a complete day, i.e. a 24 hour period.

In a second embodiment of the invention, the second charge related battery characteristic may be a charge rate of the battery. As in the case of the first embodiment of the invention, the first charge related battery characteristic, in this embodiment, may be the safety margin.

In this second embodiment of the invention, the method may include adjusting the rate of charge of the battery, rather than the degree of charge, depending on the charge level of the battery relative to the safety margin. Thus, if the charge level is lower than the safety margin, the method may include increasing the charge rate. Conversely, if the charge level is above the safety margin, the method may include decreasing the charge rate.

In respect of both embodiments, the method may include controlling the amount of charge normally stored in the battery. The amount of charge normally stored in the battery may be controlled using feedback control. For example, on a daily basis, the preset charge level (in the case of the first embodiment of the invention) or the charge rate (in the case of the second embodiment of the invention) may be adjusted. The size of the adjustment may be related to the safety margin. Typically, an adjustment step size may be approximately 1%-10% of the safety margin, more particularly, about 3%-7% of the safety margin and, optimally, about 5% of the safety margin.

Still further, the method may include adjusting the safety margin to take into account ageing of the battery. The safety margin may be automatically adjusted by characterising the battery as it ages. The method may therefore include creating a look-up table in an electronic memory of the implant that provides the safety margin point for each preset charge level or charge rate, as the case may be, so that, when the preset charge level or charge rate is updated, so is the safety margin. The table may be constructed so that the safety margin is equal to a fixed period of time.

The time represented by the safety margin may also need to be adjusted depending on the recipient's needs. The recipient or a third party may indicate the time that they require the safety margin to be set at and, by knowing the characteristics of the battery and the current drawn by the specific recipient's data map, a voltage corresponding to the safety margin desired by the recipient may be included in the electronic memory of the implant. The safety margin may be downloaded along with the recipient's map into the memory of the implant.

According to a second aspect of the invention, there is provided a control system for controlling charging of a battery of a totally implantable auditory prosthesis, the control system comprising:

a controller for controlling charging of the battery, the controller being a programmable controller having data relating to a first charge related battery characteristic and a second charge related battery characteristic and for adjusting the second charge related battery characteristic dependent upon where a charge level of the battery is relative to the first charge related battery characteristic when a charging cycle commences; and a switching arrangement for switching a charging source into charging communication with the battery when charging of the battery is required.

As in the case of the first aspect of the invention, the second charge related battery characteristic may, in accordance with one embodiment of the invention, be a preset charge level of the battery and may, in accordance with a second embodiment of the invention, be a charge rate of the battery. The first charge related battery characteristic may be the safety margin, as defined, of the battery.

In the case of the first embodiment of this aspect of the invention, the switching arrangement may be a switch controlled by the controller. The charging source may include a radio frequency (RF) link which provides charge to the battery when required and/or power to the implant. The switch may be connected between the RF link and the battery and may be closed under the action of the controller when the battery of the implant requires charging.

The control system may include an analog-to-digital converter for converting a battery voltage to a number to be fed to the controller.

The controller may store numbers corresponding to voltages that, in turn, correspond to the preset charge level, a minimum battery charge and the safety margin. The relationship between charge level and voltage is not linear but is stable so that it can be measured for the battery. A simple look-up table may be stored in a memory of the controller to be used for voltage-to-charge conversion.

The controller may detect when charging of the battery has commenced, i.e. when the switch has closed, so that the controller can determine if the preset charge level needs to be adjusted. This may be done by monitoring the RF link power periodically, for example, once per minute.

In the case of the second embodiment of the invention, the switching arrangement may comprise a switching circuit. The switching circuit may comprise a voltage-to-current converter feeding to a current amplifier and mirror. The converter may include an operational amplifier, an output of which is connected to a switch means in the form of a field effect transistor (FET). The operational amplifier may have a first, "current control" input which causes the output of the amplifier to turn the FET on. The FET may be connected between a pair of resistors. When the FET is turned on, current flows through a first resistor connected to a source of the FET. All the current also flows through the second resistor connected to a drain of the FET. Current may flow through the first resistor until the voltages at inputs of the current amplifier are equal.

Current flow through the second resistor may induce a voltage at an input of the current amplifier. A second switch means may be connected to an output of the current amplifier with the battery to be charged being connected to the second switch means. The second switch means may also be a FET.

The components of the switching arrangement may be selected so that only a small voltage differential exists between the voltage from the RF link and the battery voltage.

The charge current may be adjusted by changing the "current control" voltage. This may be done using an analog voltage or may be controlled by a digital number if a digital-to-analog converter is to be used.

In the case of the second embodiment of the invention, the switching arrangement may replace the switch of the first embodiment of the invention.

BRIEF DESCRIPTION OF THE DRAWINGS

The invention is now described by way of example with reference to the accompanying drawings in which:—

DETAILED DESCRIPTION

Figure 1:
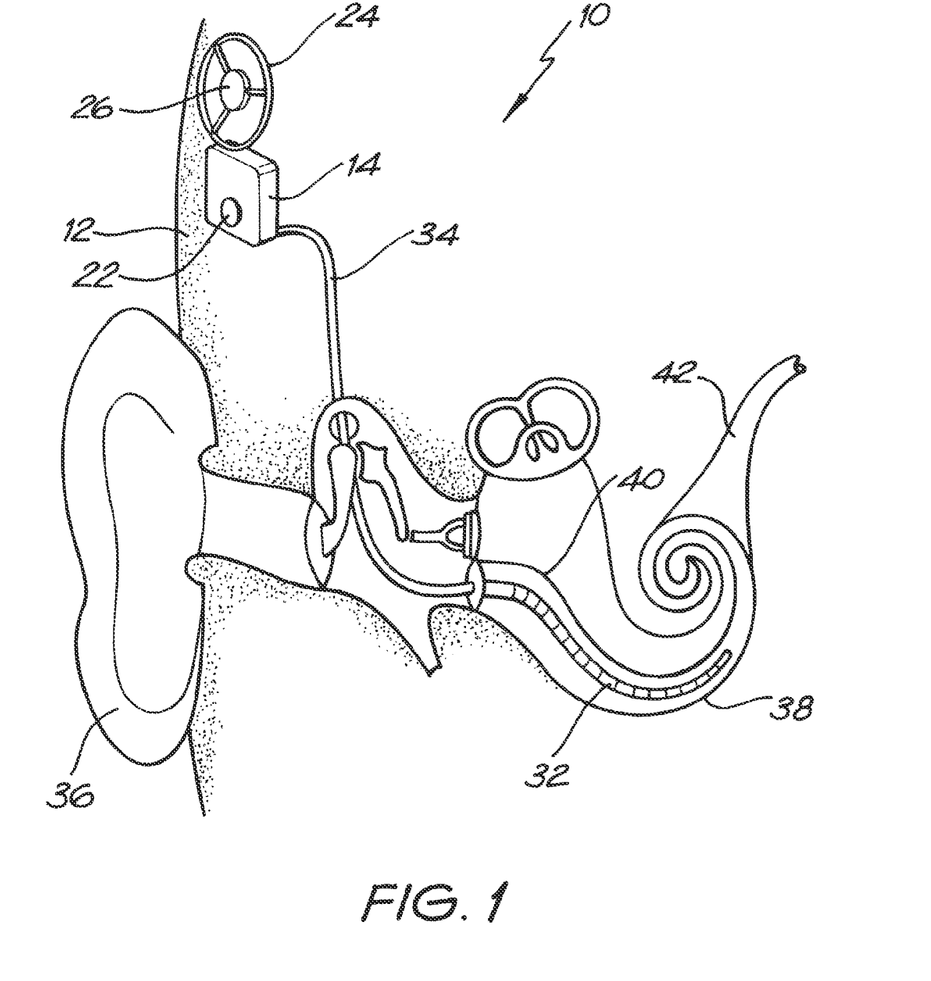
FIG. 1 shows a schematic representation of a totally implantable cochlear implant.

In FIG. 1 of the drawings, reference numeral 10 generally designates a totally implantable cochlear implant incorporating an example of the invention. The implant 10 is a self-contained unit implanted into a skull 12 of a recipient in an excavated region of a temporal bone of the recipient's skull 12.

As described in the Applicant's above referenced International Patent Application, the implant 10 is totally implanted within the recipient's skull and has no external or externally accessible components.

Figure 5:
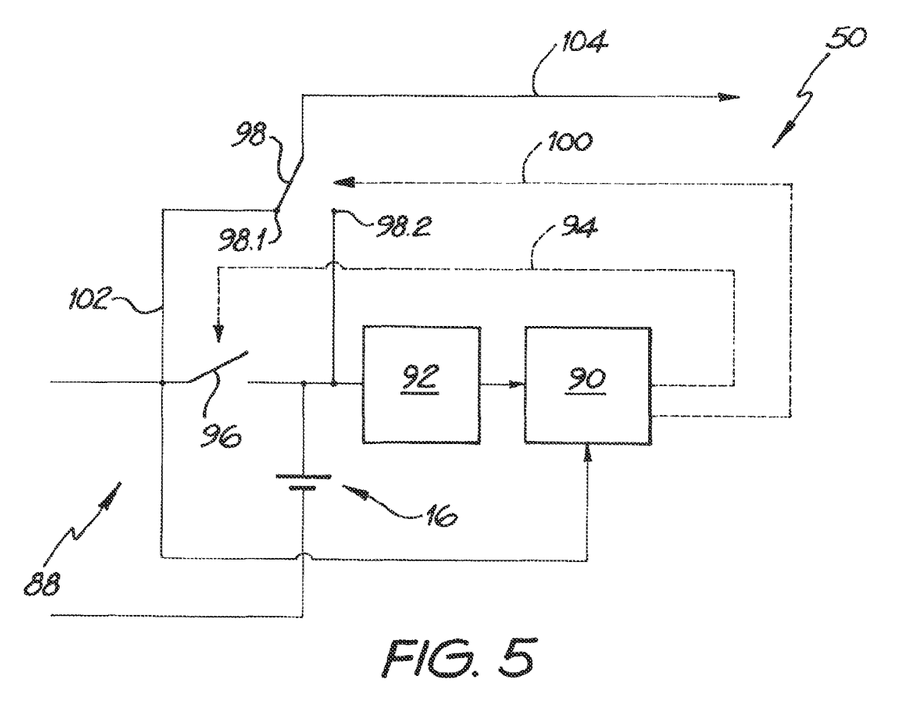
FIG. 5 shows a block diagram of a control system, in accordance with a first embodiment of the invention for charging a battery of the implant of FIG. 1.
Figure 6:
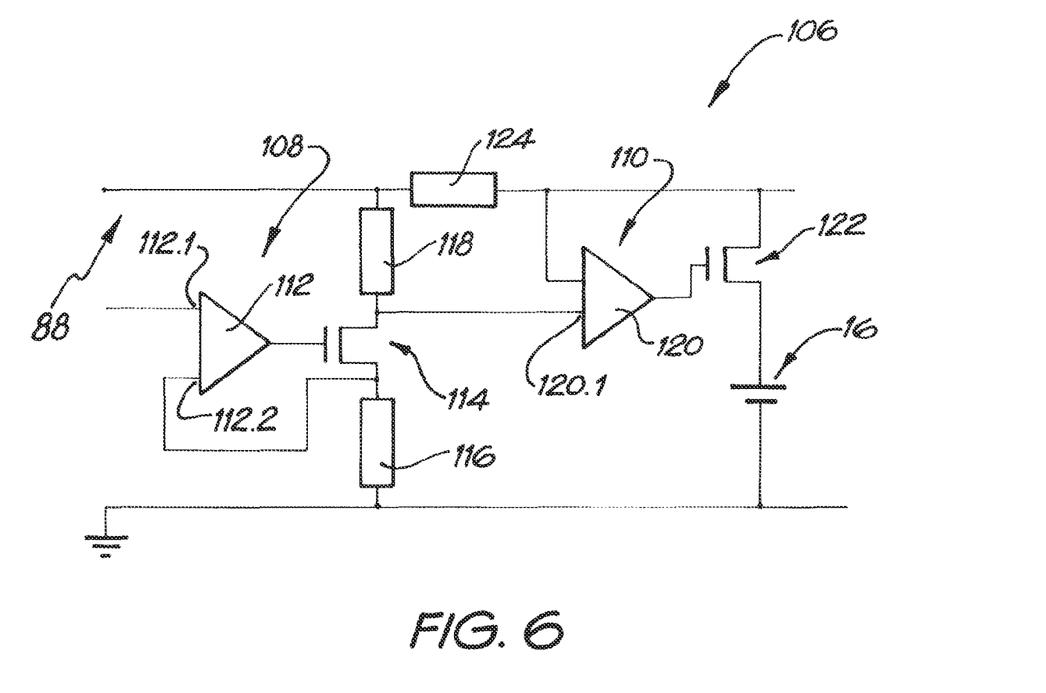
FIG. 6 shows a part of the control system, in accordance with a second embodiment of the invention, for charging the battery of the implant of FIG. 1.

The implant 10 has a hermetically sealed housing 14. The housing 14 houses a battery 16 (FIGS. 5 and 6). The housing 14 also contains electronic components of the implant 10. The electronic components include a speech processor and an electronic memory in which recipient-specific parameters are stored. In the depicted embodiment, the battery 16 is a lithium-ion battery which is rechargeable a number of times. It will be appreciated that other rechargeable battery types could be utilised.

A microphone 22 is mounted on the housing 14 for receiving external sound signals for transmission to the electronic components of the implant 10 for processing.

The implant 10 includes a receiver antenna coil 24 having a central magnet 26. The receiver antenna coil 24 is mounted externally of the housing 14 and is connected to the electronic components and the battery 16 of the implant 10 via external leads and a feedthrough (neither of which is shown).

Stimulation signals generated by the speech processor of the implant 10 are fed to an electrode array 32 via a lead 34.

In practice, the implant 10 is implanted in the recipient's skull 12 in a recess formed in the temporal bone adjacent an outer ear 36 of the recipient. The electrode array 32 is mounted in the cochlea 38 of the recipient. When stimulation signals are received by the electrode array 32 these signals are transmitted to the basilar membrane 40 to stimulate the recipient's auditory nerve 42.

The housing 14 of the implant 10 is of a biocompatible material. More particularly, the housing 14 is a hermetically sealed titanium housing. Prior to implantation, the housing 14 is coated with a layer of silicone or parylene as a further protective measure for the implant 10.

As indicated above, the battery of the implant 10 is a lithium-ion battery. Lithium-ion batteries have the advantage that they are of extremely long life and can be recharged a number of times. However, such batteries can only be charged a finite number of times before they "wear out". As a lithium-ion battery wears out, its charge storage capacity decreases. In practice, after approximately 1000 charge/discharge cycles, a lithium-ion battery may only be able to store 50% of the charge that it could in comparison to when the battery was new.

The tendency of a battery to wear out is greater if the battery is always fully charged each time it undergoes a charging cycle. Further, the wear out rate increases if high currents are used for charging a battery or discharging it.

Totally implantable cochlear implants are intended to be used with at least an external power pack for charging the battery. Often, the implant is used together with an external speech processor where the situation demands it, or it may not be necessary for an external speech processor, in which case it can be omitted. Typically, an external speech processor is used where the recipient finds himself or herself in adverse or difficult acoustic environments or at work but the implant may be used on its own without the external speech processor where cosmetic requirements and/or convenience dictate.

The external speech processor incorporates a power pack so that, when it is being used and when required, the external speech processor can be used for charging the battery 16 of the implant 10. The charging of the battery 16 takes place under the control of a control system 50 (FIG. 5), also in accordance with the invention and which will be described in greater detail below.

Optimisation of the charging of the battery 16 ensures that the number of times, during the life of the implant 10, that the implant 10 needs to be explanted and/or re-implanted for battery replacement is reduced.

In accordance with a first embodiment of the invention, the charging of the battery is controlled so that the battery is charged to a level below a maximum charge level 52 (see FIGS. 2 and 3 of the drawings).

In addition, a first battery charge related characteristic, referred to as a "safety margin" is selected. The safety margin, designated at 58 in FIGS. 2 to 4 of the drawings, is a charge level greater than a minimum battery charge level 60. The minimum battery charge level is a level below which the battery 60 will not function.

A second battery charge related characteristic is also selected. In the case of the first embodiment of the invention, the second battery charge related characteristic is a preset charge level 62.

In the drawings, it is assumed that the person uses the external speech processor (not shown) for approximately 12 hours per day and runs the implant 10 on its internal battery 16 for the remaining 12 hours of the day. When the external speech processor is in use, the battery 16 is able to be charged. In FIG. 2 of the drawings, two curves 64 and 66 are shown. In the case of the first curve 64, during the day, the battery 16 is charged by the external speech processor until it reaches the preset charge level 62. While the implant 10 is running on its internal battery 16, during the night, the battery 16 discharges to a level 68. It is to be noted that the level 68 is a charge level exceeding the safety margin 58. Accordingly, the control system 50 reduces the preset charge level as shown at 70 so that, when the external speech processor is applied the following day, the battery 16 is charged to a lower level than the preceding day. When the battery charge reaches the preset charge level 62, the control system 50 ceases charging of the battery 16 as shown by plateau 72 of the curve 64. Because the internal battery 16 of the implant 10 is not being used, the battery charge remains at the plateau 72 until the external speech processor is disconnected whereafter the implant 10 again runs on the battery 16 causing it to discharge.

Figure 2:
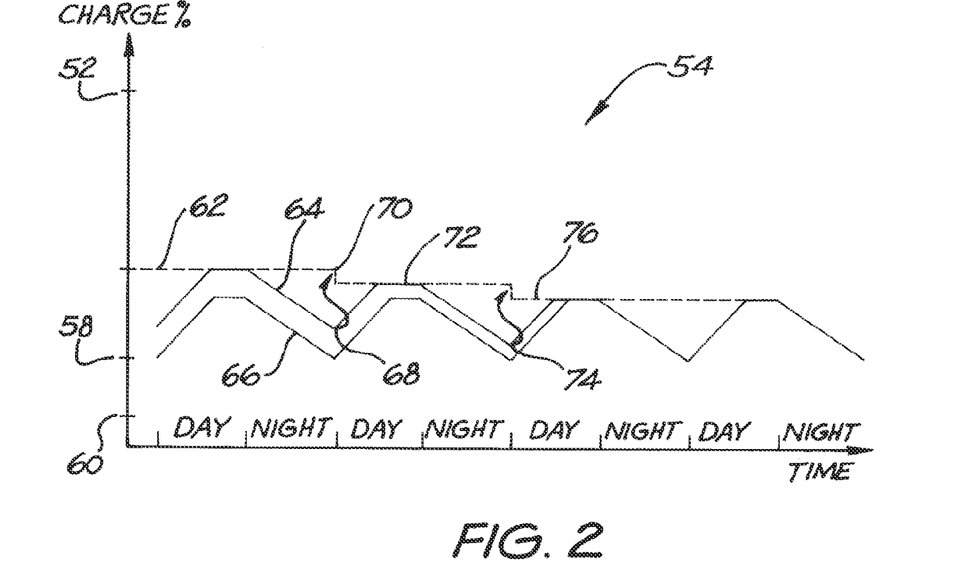
FIGS. 2 and 3 show graphs of charge versus time for a method of charging a battery of the implant, in accordance with a first embodiment of the invention.

The battery 16 discharges during the night to a level as shown at 74 in FIG. 2 of the drawings. Once again, this level is greater than the safety margin 58 so that the following day, when the external speech processor is reapplied to start charging the battery 16, the control system 58 resets the preset charge level to a yet lower level as shown at 76. When the battery reaches charge level 76, the control system 50 causes charging of the battery 16 to stop.

Curve 66 shows the ideal situation where the battery always discharges to the safety margin 58. As a result, there is no need to adjust the preset charge level 62.

Figure 3:
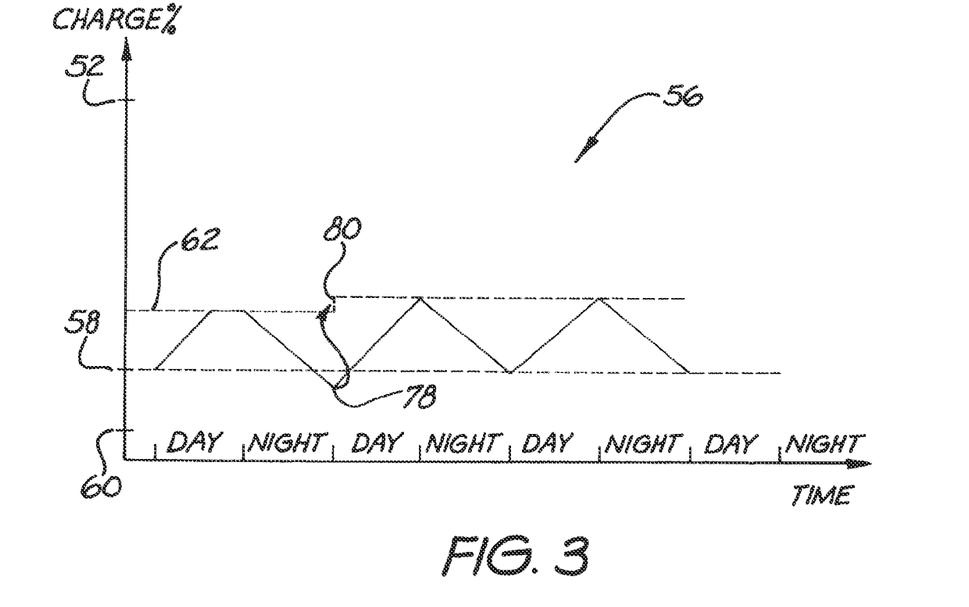

FIG. 3 shows the situation where, during running of the implant on the internal battery 16 during the first night of a period, the battery discharges to a level below the safety margin, as shown at 78 in FIG. 3 of the drawings. Because this has occurred, the following day, when the external speech processor is applied, the control system 50 adjusts the preset charge level 62 upwardly as shown at 80 in FIG. 3 of the drawings. In this case, only one adjustment is needed as, in the following night, when the implant is running on its battery 16, the battery 16 discharges to the safety margin 58 and no adjustment of the preset charge level 62 is thereafter required.

Figure 4:
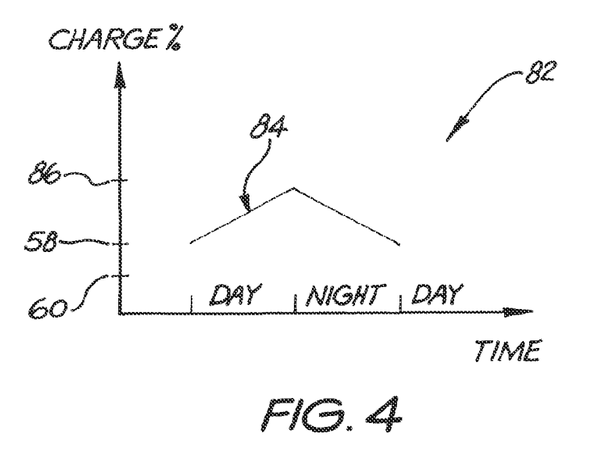
FIG. 4 shows a part of a graph of charge versus time for a method of charging a battery of the implant, in accordance with a second embodiment of the invention.

Referring now to FIG. 4 of the drawings, a further curve 82 of a second embodiment of the invention for controlling charging of a battery of the implant 10 is illustrated. With reference to FIGS. 2 and 3 of the drawings, like reference numerals refer to like parts, unless otherwise specified.

In this embodiment of the invention, rather than adjusting the degree of charge of the battery 16, the rate of charge of the battery 16 is adjusted. Regardless of the embodiment of the invention, the charging of the battery takes place such that the battery is not charged to its maximum level 52.

During the day, when the external speech processor is applied, the battery 16, should it require charging, is charged at a predetermined rate as shown at 84. The rate at which the battery 16 is charged is dependent on where the charge level of the battery 16 was at the time of commencement of charging of the battery 16 at the start of a charging cycle. If the charge level of the battery 16 was below the safety margin, the charge rate of the battery 16 is increased until a desired charge level, as shown at 86, is reached.

If the charge level of the battery 16 is above the safety margin, the charge rate of the battery 16 is decreased.

Referring now to FIG. 5 of the drawings, the control system 50 is described in greater detail. The control system 50 forms part of the electronic components contained within the housing 14 of the implant 10.

As indicated above, the battery 16 is charged via a radio frequency (RF) link 88 from the external speech processor. The control system 50 includes a controller 90. The controller 90 is microprocessor based and includes an electronic memory. The electronic memory stores the safety margin 58 and the preset charge level 62 therein. The battery voltage is monitored and is converted to a number by an analog-to-digital converter 92. The number representing the battery voltage is fed to the controller 90 from the converter 92. The system 50 works on a feedback basis and includes a feedback loop 94 controlling a normally open switch 96. The switch 96 is controlled by the controller 90 so that, when the battery 16 is to be charged, the switch 96 is closed and when the battery 16 is not to be charged, the switch 96 is open.

Power transmitted through the link 88 is also fed to the controller 90 so that the controller 90 detects when this "RF power" is present. When RF power is present via the link 88, the controller 90 controls a toggle switch 98, via a control line 100 to switch a wiper of the switch 98 to contacts 98.1 to connect a line 102 to the implant 10 via a line 104. Power is therefore supplied from the link 88 to the implant 10 on the line 104. When the controller 90 detects that the link 88 is absent, the controller 90 switches the wiper of the switch 98 to contacts 98.2 so that the implant 10 is powered from the on-board battery 16.

The preset charge level 62, the safety margin 58 and the minimum battery charge level 60 are all stored as numbers in the controller 90. The relationship between charge and battery voltage is not linear but is stable so that it can be measured for the battery 16 and a simple look-up table is used for voltage-to-charge conversions.

The controller 90 detects when charging of the battery 16 has started so it can determine if the preset charge level 62 needs to be adjusted. The controller 90 monitors the link power periodically, for example, every one minute.

In the case of the second embodiment of the invention, the switch 96 is replaced by a switching arrangement 106 (FIG. 6 of the drawings). The switching arrangement 106 includes a voltage-to-current converter 108 connected to a current amplifier and mirror 110.

The converter 108 includes an operational amplifier 112 having a pair of inputs 112.1 and 112.2. The input 112.1 is a current control input. A voltage at the current control input 112.1 causes the output of the operational amplifier 112 to turn on a switch in the form of a field effect transistor (FET) 114. When the FET 114 turns on, current flows through a first resistor 116, connected to a source of the FET 114 until the voltages at the inputs 112.1 and 112.2 of the amplifier are equal. All the current flowing through the first resistor 116 also flows through a second resistor 118 connected to a drain of the FET 114. This induces a voltage at input 120.1 of an operational amplifier 120 of the amplifier 110. When this occurs the operational amplifier 120 turns on a second switch in the form of an FET 122 until the voltage across a third resistor 124 equals that across the second resistor 118. This then generates a charge into the battery 16.

The circuit 106 provides a stable charge current. If suitably low values of resistors 118 and 124 are selected, this allows the battery 16 to be charged with only a small voltage differential between the voltage from the link 88 and the battery voltage 16. The charge current, i.e. the rate at which the battery 16 is charged, can be adjusted by adjusting the voltage applied at input 112.1 of the operational amplifier 112. This may be done by using an analog voltage or may be controlled by a digital number if a digital-to-analog converter is used.

As described above, the circuit 106 replaces the switch 96 in the system 50 in the case of the second embodiment of the invention, i.e. when the battery charge rate is adjusted rather than the degree of charge of the battery.

In the case of the second embodiment of the invention, it is not necessary to monitor the maximum voltage to which the battery charges except to ensure that it is not overcharged. However, it is still necessary to measure the minimum voltage so that the amount of charge delivered is controlled.

As described above, the control system 50 uses feedback to control the amount of charge normally stored by the battery. On a daily basis, the preset charge level 62, or the charge rate, as the case may be, are adjusted. The degree of adjustment needs to be determined. A large adjustment would correspond to a high loop gain. If the adjustment were too large, then the power charge cycle would become erratic due to the minor differences in day-to-day use. Conversely, if the adjustment were too small, the system 50 could not keep track of changing battery characteristics. As battery characteristics change slowly, a slow change is all that is required.

A small adjustment ensures that the charge levels are based on the average use over an extended period of time rather than a single day, which may prove to be anomalous in use. Typically, a step size adjustment of approximately 5% of the safety margin 58 is regarded as satisfactory.

As the battery 16 ages, its safety margin 58 gets smaller. In other words, the time taken by the system to discharge the battery from the safety margin 58 position to a point where the battery is fully discharged will decrease. In an extreme case, it is possible that the time could be so short that if the recipient had a particularly long time of powering the device from the external battery, the implanted battery 16 may run out of power and the implant 10 could stop working. As a result, the safety margin 58 itself is adjustable. Data relating to the safety margin 58 are included in the recipient's map parameters for their implant.

The safety margin 58 could also be automatically adjusted. This is effected by characterising the battery 16 as it ages. A look up table is created that provides the safety margin 58 for each preset charge level 62 or charge rate, as the case may be, so that, when the preset charge level or charge rate is updated, so is the safety margin 58.

The time represented by the safety margin 58 might also need to be adjusted depending on the recipient's needs. The recipient or a third party can indicate the time in hours that they want the safety margin to be. By knowing the battery characteristics, i.e. the relationship between the charge held by the battery 16 and the battery voltage, and the current drawn by the specific recipient's map, the voltage corresponding to the safety margin 58 as desired by the recipient is included in an electronic memory of the implant 10. This value is loaded along with the recipient's map using conventional implant programming techniques.

In another manner of adjusting the safety margin, the voltage corresponding to the safety margin 58 is measured by asking the recipient to use the implant until it stops working because the battery 16 is fully discharged. A clock within the implant 10 causes the battery voltage to be measured periodically, say every hour, and is stored. From this data the voltage corresponding to the desired safety margin required by the recipient are determined It will be appreciated that, rather than automatically controlling the charging of the battery, the control of the charge of the battery could be manually effected. In such a case, the battery voltage is monitored and is telemetered out of the implant 10 to an external controller such as a hand-held computer or similar device. The external controller includes a manual display that the recipient can use to judge the amount of charge in the battery 16. The external controller also includes commands that the recipient or a third party uses to select either the charge rate or the maximum amount of charge in the battery 16. The system works in the same way as the automatic control system except that the recipient is required to adjust the charge parameters.

It is a particular advantage of the invention that, because the battery 16 is not charged to its maximum charge level and is not charged at a maximum charging rate, the life of the battery 16 is considerably extended in comparison with batteries charged using conventional charging techniques. The advantage of this is that the number of times that the implant 10 needs to be explanted for battery replacement is considerably reduced. Thus, trauma to the recipient in having to undergo surgery is reduced. It will be appreciated that, particularly with a recipient of relatively advanced age, this has major benefits. As the method of charging the battery is implemented largely by software, the complexity of the implant is not significantly increased. As a result, the reliability of the implant should not be adversely affected.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A control system for controlling charging of a battery of a totally implantable auditory prosthesis, the control system comprising:
   a controller for controlling charging of the battery, the controller being a programmable controller having data relating to a first charge related battery characteristic and a second charge related battery characteristic and for adjusting the second charge related battery characteristic dependent upon where a charge level of the battery is relative to the first charge related battery characteristic when a charging cycle commences,
   wherein the first charge related battery characteristic is a desired minimum amount of battery charge after a time period during which the battery discharges, and the second charge related battery characteristic is a preset charge level.

2. The control system of claim 1, which includes a switching arrangement for switching a charging source into charging communication with the battery when charging of the battery is required, and wherein the switching arrangement is a switch controlled by the controller.

3. The control system of claim 2, wherein the charging source includes a radio frequency (RF) link which provides charging to the battery when required and/or power to the implant.

4. The control system of claim 3, wherein the switch is connected between the RF link and the battery and is closed under the action of the controller when the battery of the implant requires charging.

5. The control system of claim 1, wherein the control system includes an analog-to-digital converter for converting a battery voltage to a number to be fed to the controller.

6. The control system of claim 1, wherein the controller detects when charging of the battery has commenced.

7. The control system of claim 1, wherein the auditory prosthesis is a cochlear implant.

8. The control system of claim 1, wherein the second charge related battery characteristic is adjusted using feedback control.

9. The control system of claim 1, wherein adjusting the preset charge level comprises:
   adjusting the preset charge to a level that is lower than a maximum charge of the battery.

10. The control system of claim 1, wherein adjusting the preset charge level comprises:
    reducing the preset charge level by a specified amount when the battery charge level exceeds the desired minimum amount.

11. The control system of claim 1, wherein adjusting the preset charge level comprises:
    increasing the preset charge level by a specified amount when the battery charge level is below the desired minimum amount.

12. The control system of claim 1, wherein the controller is configured to adjust the desired minimum amount.

13. The control system of claim 12, wherein the desired minimum amount is automatically altered when the second battery characteristic is altered based on a corresponding value in a look up table.

14. The control system of claim 12, wherein the desired minimum amount is manually altered.

15. The control system of claim 1, wherein adjusting the second charge related battery characteristic provides an adjusted second charge related battery characteristic, the method further comprising:
- detecting when a second charge cycle of the battery commences;
- measuring the battery charge level when the second charge cycle commences;
- determining the difference between the battery charge level and the desired minimum amount when the second charge cycle commences; and
- adjusting the adjusted second charge related battery characteristic based on the difference between the battery charge level and the desired minimum amount at the commencement of the second charge cycle.

16. The control system of claim 1, wherein the second charge related battery characteristic is adjusted at commencement of a first charge cycle, said adjustment comprising: increasing the second charge related battery characteristic by a specified amount to provide an adjusted second charge related battery characteristic.

17. The control system of claim 16, wherein the second charge related battery characteristic is adjusted at commencement of a second charge cycle, said adjustment comprising: increasing the adjusted second charge related battery characteristic by the specified amount.

18. A control system for controlling charging of a battery of a totally implantable auditory prosthesis, the control system comprising:
- a controller for controlling charging of the battery, the controller being a programmable controller having data relating to a first charge related battery characteristic and a second charge related battery characteristic and for adjusting the second charge related battery characteristic dependent upon where a charge level of the battery is relative to the first charge related battery characteristic when a charging cycle commences, wherein the first charge related battery characteristic is a desired minimum amount of battery charge after a time period during which the battery discharges, and the second charge related battery characteristic is a preset charge level; and
- a switching arrangement for switching a charging source into charging communication with the battery when charging of the battery is required.

* * * * *